US007824404B2

(12) United States Patent
Godara et al.

(10) Patent No.: US 7,824,404 B2
(45) Date of Patent: Nov. 2, 2010

(54) METHODS OF TREATING THE SACROILIAC REGION OF A PATIENT'S BODY

(75) Inventors: Neil Godara, Mississauga (CA); Wesley Dawkins, Toronto (CA); Taylor Hillier, Etobicoke (CA); Mark Leung, Toronto (CA)

(73) Assignee: Kimberly-Clark, Inc., Mississauga, Ontario (CA)

( * ) Notice: Subject to any disclaimer, the term of this patent is extended or adjusted under 35 U.S.C. 154(b) by 657 days.

(21) Appl. No.: 11/534,907

(22) Filed: Sep. 25, 2006

(65) Prior Publication Data

US 2007/0055316 A1 Mar. 8, 2007

Related U.S. Application Data

(62) Division of application No. 11/280,604, filed on Nov. 15, 2005.

(60) Provisional application No. 60/595,560, filed on Jul. 14, 2005, provisional application No. 60/595,559, filed on Jul. 14, 2005, provisional application No. 60/595,426, filed on Jul. 4, 2005, provisional application No. 60/594,787, filed on May 5, 2005, provisional application No. 60/593,839, filed on Feb. 17, 2005, provisional application No. 60/627,813, filed on Nov. 15, 2004.

(51) Int. Cl.
*A61B 18/18* (2006.01)

(52) U.S. Cl. ............................. 606/41; 606/42; 606/43; 606/44; 606/45

(58) Field of Classification Search ............. 606/32–45; 607/17
See application file for complete search history.

(56) References Cited

U.S. PATENT DOCUMENTS

| 4,612,934 | A | 9/1986 | Borkan |
| 5,342,357 | A | 8/1994 | Nardella |
| 5,397,338 | A | 3/1995 | Grey et al. |
| 5,951,546 | A | 9/1999 | Lorentzen |
| 6,002,964 | A | 12/1999 | Feler et al. |
| 6,104,957 | A | 8/2000 | Alo et al. |
| 6,146,380 | A * | 11/2000 | Racz et al. ................ 606/41 |
| 6,277,112 | B1 * | 8/2001 | Underwood et al. ......... 606/32 |

(Continued)

FOREIGN PATENT DOCUMENTS

| WO | 81/03272 | 11/1981 |
| WO | 94/02077 | 2/1994 |
| WO | 95/10320 | 4/1995 |
| WO | 98/19613 | 5/1998 |
| WO | 99/43263 | 9/1999 |

OTHER PUBLICATIONS

Steven P. Cohen et al., "Lateral Branch Blocks as a Treatment for Sacroiliac Joint Pain: A Pilot Study", (Mar.-Apr.), 2003, Regional Anesthesia and Pain Medicine, vol. 28, No. 2, pp. 113-119.*

(Continued)

*Primary Examiner*—Linda C Dvorak
*Assistant Examiner*—Amanda Scott
(74) *Attorney, Agent, or Firm*—Dority & Manning, P.A.

(57) ABSTRACT

Methods of treating the sacroiliac region of a patient's body by delivering energy are described. In some embodiments, the method comprises the steps of: positioning one elongated probe comprising at least one energy delivery device within a sacroiliac joint of the body; and delivering radiofrequency energy through the elongated probe. In some embodiments, the delivery of energy results in the creation of a lesion. In further embodiments, energy may be delivered substantially along a long axis of the sacroiliac joint. In yet further embodiments, at least one energy delivery device may be positioned adjacent a sacroiliac joint and energy may be delivered so as to create a lesion at least partially within the joint.

36 Claims, 5 Drawing Sheets

U.S. PATENT DOCUMENTS

| | | | |
|---|---|---|---|
| 6,379,349 | B1 | 4/2002 | Müller et al. |
| 6,562,033 | B2 * | 5/2003 | Shah et al. ............... 606/41 |
| 6,735,474 | B1 | 5/2004 | Loeb et al. |
| 6,847,849 | B2 | 1/2005 | Mamo et al. |
| 2002/0120260 | A1 | 8/2002 | Morris et al. |
| 2002/0147485 | A1 | 10/2002 | Mamo et al. |
| 2004/0199161 | A1 | 10/2004 | Truckai et al. |
| 2004/0215287 | A1 | 10/2004 | Swoyer et al. |
| 2005/0033372 | A1 | 2/2005 | Gerber |
| 2005/0085806 | A1 | 4/2005 | Auge, II et al. |
| 2005/0096718 | A1 | 5/2005 | Gerber et al. |
| 2005/0177209 | A1 | 8/2005 | Leung et al. |
| 2005/0240238 | A1 | 10/2005 | Mamo et al. |
| 2006/0020297 | A1 | 1/2006 | Gerber et al. |

OTHER PUBLICATIONS

F. Michael Ferrante et al., "Radiofrequency Sacroiliac Joint Denervation for Sacroiliac Syndrome", (Mar.-Apr.), 2001, Regional Anesthesia and Pain Medicine, vol. 26, No. 2, pp. 137-142.*
Valleylab-RF Pain Management System; Sep. 16, 2004; http://www.valleylab.com/static/pain/products-generator.html.*
Cohen, Steven P. 'Sacroiliac Joint Pain: A Comprehensive Review of Anatomy, Diagnosis, and Treatment'. Anesth Analg Nov. 2005:101:1440-53.
Buijs EJ, Kamphuis ET, Groen G.J. "Radiofrequency treatment of sacroiliac joint-related pain aimed at the first three sacral dorsal rami: A minimal approach". Pain Clinic. 16(2):139-146. 2004.
Jiang J., Xiao L.Z., Zheng H.S., Zhu H.Q. "Comparison between radiofrequency coagulation plus small needle knife and single method in treatment of sacrolumbar pain". Chinese Journal of Clinical Rehabilitation. 7(20): 2844-2845. 2003.
Plancarte RS, Mayer-Rivera FJ. "Radiofrequency Procedures for Sacral and Pelvic Region Pain". Pain Practice. 2(3):248-249 (2002).
Fukui S, Nosaka S. "Succesful relief of hip joint pain by percutaneous radiofrequency nerve thermocoagulation in a patient with contraindications for hip arthroplasty". J Anesth. 15(3):173-175 (2001).
Cohen SP, Foster A. "Pulsed radiofrequency as a treatment for groin pain and orchialgia". Urology. 61(3):645 (2003).
Kawaguchi M, Hashizume K, Iwata T, Furuya H. "Percutaneous radiofrequency lesioning of sensory branches of the obturator and femoral nerves for the treatment of hip joint pain". Reg Anesth Pain Med. 26(6):576-581 (2001).
Akatov OV, Dreval ON. "Percutaneous radiofrequency destruction of the obturator nerve for treatment of pain caused by coxarthrosis". Stereotact Funct Neurosurg. 69(1-4 Pt 2): 278-280 (1997).
Ferrante FM, Aranda M, Delaney LR, Kim PS, King LF, Mannes AJ, Mardini IA, Roche EA. "Radiofrequency sacroiliac joint denervation for sacroiliac syndrome". Reg Anesth Pain Med. 26(2):137-142 (2001).
Gopalani AF, Malik A, Simopolous T. "A novel technique for treating nonsurgical hip pain with radiofrequency lesioning of the sensory branches of the obturator and femoral nerves: a case report". Archives of Physical Medicine and Rehabilitation. 84(9): E23 (2003).
Pino CA, Hoeft MA, Hofsess C, Rathmell JP. "Morphologic analysis of bipolar radiofrequency lesions: implications for treatment of the sacroiliac joint". Reg Anesth Pain Med. 30(4):335-338 (2005).
Yin W, Willard F, Carreiro J, Dreyfuss P. "Sensory stimulation-guided sacroiliac joint radiofrequency neurotomy: technique based on neuroanatomy of the dorsal sacral plexus". Spine. 28(20):2419-2425 (2003).
Ahadian, FM. "Pulsed radiofrequency neurotomy: advances in pain medicine". Curr Pain Headache Rep. 8(1):34-40 (2004).
Gevargez A, Groenemeyer D, Schirp S, Braun M. "CT-guided percutaneous radiofrequency denervation of the sacroiliac joint". Eur Radiol. 12(6)1360-1365 (2002).
Anis N, Chawki N, Antoine K. "Use of radio-frequency ablation for the palliative treatment of sacral chordoma". AJNR. 25(9):1589-1591 (2004).
Conaghan P, Farouk R. "Sacral nerve stimulation can be successful in patients with ultrasound evidence of external anal sphincter disruption". Diseases of the Colon and Rectum. 48(8):1610-1614.
Kirsch DG, Ebb DH, Hernandez AH, Tarbell NJ. "Proton radiotherapy for Hodgkin's disease in the sacrum". Lancet Oncology. 6(7):532-533 (2005).
Leng WW, Chancellor MB. "How sacral nerve stimulation neuromodulation works". Urol Clin North Am. 32(1):11-8 (2005).
Kirkham APS, Knight Sl, Craggs MD, Casey ATM, Shah PJR. "Neuromodulation through sacral nerve roots 2 to 4 with a Finetech-Brindley sacral posterior and anterior root stimulator". Spinal Cord. 40(6):272-281 (2002).
Simon S. "Sacroiliac joint injection and low back pain". Interventional Pain Management. 636-539 (2001).
Kline MT, Yin W. "Radiofrequency techniques in clinical practice". Interventional Pain Management. 243-290 (2001).
Cole AJ, Dreyfuss P, Stratton SA. "The Sacroiliac Joint: A Functional Approach". Critical Reviews in Physical and Rehabilitation Medicine. 8(1&2):125-152 (1996).
Atlihan D, Tekdemir I, Ates Y, Elhan A. "Anatomy of the Anterior Sacroiliac Joint With Reference to Lumbosacral Nerves". Clinical Orthopaedics and Related Research. 376: 2360241 (2000).
Calvillo O, Skaribas I, Turnipseed J. "Anatomy and Pathophysiology of the Sacroiliac Joint". Current Review of Pain. 4:356-361 (2000).
Davies PW, Luthardt F, Statts PS. "Radiofrequency Treatment in the United States". Pain Practice. 2(3): 192-194 (2002).
Ebraheim NA, Lu J, Biyani A, Yeasting RA. "Anatomic Considerations for Posterior Approach to the Sacroiliac Joint". Spine. 21(23): 2709-2712 (1996).
Fortin JD, Washingtion WJ, Falco FJE. "Three Pathways between the Sacroiliac Joint and Neural Structures". Am J Neruoradiol. 20:1429-1434 (1999).
Fortin FD, Kissling RO, O'Connor BL, Vilensky JA. "Sacroiliac Joint Innervation and Pain". The American Journal of Orthopedics.
Liguoro D, Viejo-Fuertes D, Midy D, Guerin J. "The Posterior Sacral Foramina: An Anatomical Study". J. Anat. 195:301-304 (1999).
Murata Y, Takahashi K, Yamagata M, Takahashi Y, Shimada Y, Moriya H. "Origin and pathway of sensory nerve fibers to the ventral and dorsal sides of the sacroiliac joint in rats". Journal of Orthopaedic Research. 19:379-383 (2001).
Prithvi Raj P, Erdine S. "The Current Status of the Practice of Radiofrequency in the World". Pain Practice. 2(3):176-179 (2002).
Slipman CW, Whyte WS, Chow DW, Chou L, Lenrow D, Ellen M. "Sacroiliac Joint Syndrome". Pain Physician. 4(2):143-152 (2001).
Van Zundert J, Raj P, Erdine S, van Kleef M. "Application of Radiofrequency Treatment in Practical Pain Management: State of the art". Pain Practice. 2(3):269-278 (2002).
Dreyfuss P, Rogers CJ. "Radiofrequency Neurotomy of the Zygapophyseal and Sacroiliac Joints". Pain Proc. 2 (Chapter 32): 395-420 (2000).
Deer, T. "Injections for the Diagnosis and Treatment of Spinal Pain". American Society of Anesthesiologists 32(Chapter 6):52-69 (2004).
Office Action for U.S. Appl. No. 11/280,604 "Mailed on Dec. 8, 2009".
Office Action for U.S. Appl. No. 11/280,604, "Mailed on May 12, 2009".
Response to Office Action for U.S. Appl. No. 11/280,604, "Mailed on May 12, 2009" Mailed on Dec. 11-12, 2009.
Office Action for U.S. Appl. No. 11/381,783, "Mailed on Dec. 24, 2009".
Office Action for U.S. Appl. No. 11/356,706 "Mailed on Feb. 12, 2009".
Office Action Response for U.S. Appl. No. 11/356,706 dated May 12, 2009.
Office Action for U.S. Appl. No. 11/356,706 "Mailed on Jul. 28, 2009".
Office Action Response for U.S. Appl. No. 11/356,706 dated Jan. 28, 2010.
International Search Report (PCT/CA2006/001163) - 7 pages.
International Search Report (PCT/CA2006/000229) - 4 pages.

* cited by examiner

METHODS OF TREATING THE SACROILIAC REGION OF A PATIENT'S BODY

REFERENCES TO PARENT AND CO-PENDING APPLICATIONS

This application is a divisional application of, and claims priority from, U.S. patent application publication No. 2006/0106376, which claims the benefit of: U.S. provisional application No. 60/627,813, filed Nov. 15, 2004; U.S. provisional application No. 60/593,839, filed Feb. 17, 2005; U.S. provisional application No. 60/594,787, filed May 5, 2005; U.S. provisional application No. 60/595,426, filed Jul. 4, 2005; U.S. provisional application No. 60/595,559, filed Jul. 14, 2005; and U.S. provisional application No. 60/595,560, filed Jul. 14, 2005. The aforementioned applications are all herein incorporated by reference.

TECHNICAL FIELD

The invention relates to methods of treating the sacroiliac region of a patient's body via the delivery of energy.

BACKGROUND OF THE ART

Ferrante et al. (Radiofrequency Sacroiliac Joint Denervation for Sacroiliac Syndrome; Regional Anaesthesia and Pain Medicine, Vol. 26, No. 2, pp. 137-142, March-April 2001, which is incorporated herein by reference) describe the creation of a strip lesion along the long axis of the posterior sacroiliac (SI) joint using RF energy. Multiple probes are inserted along the joint margin and energy is delivered in a bipolar configuration. Such an approach requires multiple probe insertions and requires relatively precise probe placement in order to ensure adequate lesioning between the bipolar probes. Gevargez et al. (CT-Guided Percutaneous Radiofrequency Denervation of the Sacroiliac Joint; Eur Radiol (2002) 12:1360-1365, which is incorporated herein by reference) describe the creation of a strip lesion through the interosseous ligament surrounding the SI joint using RF energy. This approach, as detailed therein, requires multiple energy delivery and repositioning steps and does not allow for the creation of a lesion within the intra-articular space of the SI joint itself. Yin et al. (Sensory Stimulation-Guided Sacroiliac Joint Radiofrequency Neurotonomy: Technique based on Neuroanatomy of the Dorsal Sacral Plexus; (2003) SPINE, Vol. 28, No. 20, pp. 2419-2425, which is incorporated herein by reference) advocate lesioning a single branch of a sacral nerve as it exits the sacral foramina. The procedure described by Yin et al. may require a relatively skilled user due to the approach involved. In addition, the procedure detailed therein is time consuming as it involves multiple steps of probe re-positioning and neural stimulation in order to locate a single symptomatic nerve branch. Furthermore, this procedure does not allow for the creation of a strip lesion nor does it allow for the creation of a lesion within the SI joint. Thus, it would be desirable to have a procedure to treat the SI region using energy delivery that overcomes some or all of the limitations of the prior art.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Definitions

In the context of the present invention, a 'strip lesion' refers to a lesion which is elongate, i.e. its length substantially exceeds at least one of its other two dimensions. A strip lesion may be substantially straight or curved.

Furthermore, in the context of the present invention, 'ablate,' ablating or 'ablation' is defined as: raising the temperature of a tissue such that at least a portion of the tissue is coagulated and a lesion is formed within the tissue.

In addition, in the context of the present invention, the term 'probe' is used to describe any elongate device comprising an energy delivery device which may be percutaneously inserted into a patient's body. These devices include but are not limited to catheters, cannulae and electrosurgical probes. For the sake of clarity, the term 'probe' is used throughout the specification to describe any such device.

Pain or other symptoms (described below) associated with or emanating from the sacroiliac region, including the SI joint and the surrounding region, have been referred to in the literature as sacroiliac syndrome, sacroiliac joint dysfunction or sacroiliac joint complex (SIJC) pain, amongst other terms, and, for clarity, will be referred to throughout this specification as sacroiliac joint syndrome (SIJS). Symptoms of sacroiliac joint syndrome may include, but are not limited to: pain, stiffness and tingling.

Finally, with respect to the present invention, the term 'proximal' is used to refer to a portion or region of a device or tissue that is located closest to the user of the device. 'Distal' refers to a portion or region of a device or tissue that is located closest to a treatment site or furthest away from the user.

With specific reference now to the drawings in detail, it is stressed that the particulars shown are by way of example and for purposes of illustrative discussion of embodiments of the present invention only, and are presented in the course of providing what is believed to be the most useful and readily understood description of the principles and conceptual aspects of the invention. In this regard, no attempt is made to show structural details of an apparatus capable of performing the method of the invention in more detail than is necessary for a complete understanding of the invention, the description taken with the drawings making apparent to those skilled in the art how the several forms of the invention may be embodied in practice.

Anatomy

Figure 1:
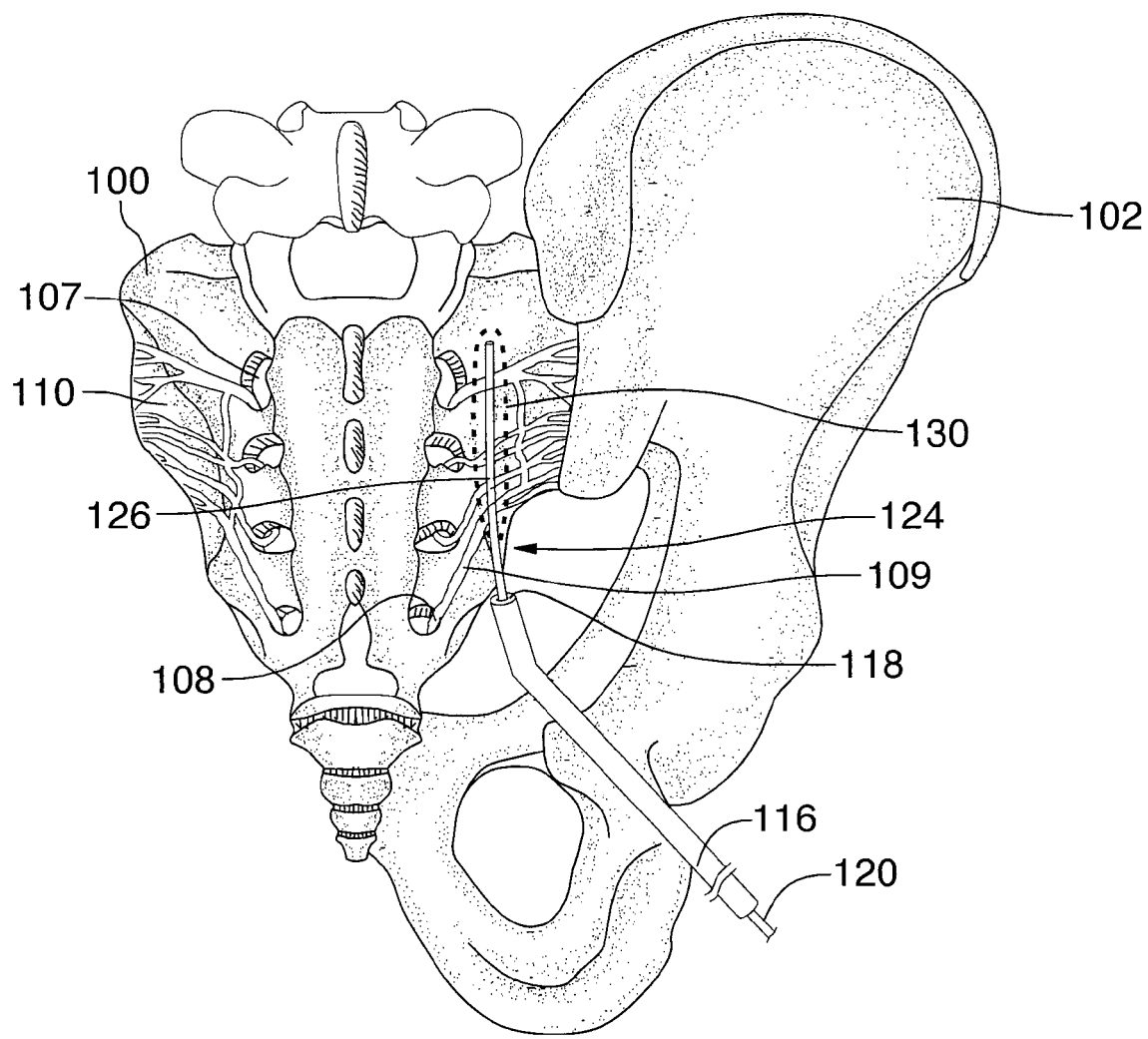
FIG. 1 is an illustration of anatomical structures in the sacroiliac region of a patient, showing the position of a probe in one embodiment of the present invention.

Referring to FIG. 1, the SI joint 110 is the joint between the sacrum 100, a large bone at the base of the spine composed of five fused vertebrae, and the ilium 102 of the pelvis. SI joint 110 is a relatively immobile joint, serving to absorb shock during locomotion. The structure of the SI joint and surrounding tissues varies significantly between individuals but generally comprises an articular cartilaginous surface, a ligamentous aspect and, in most cases, one or more synovial recesses. Though the specific pathways of SI joint innervation have not yet been elucidated, the nerves responsible for SI pain are thought to comprise, at least in part, nerves emanating from the dorsal sacral plexus, the network of nerves on the posterior surface of the sacrum, extending from the sacral nerves 108, also referred to as the posterior primary rami 108, that exit the sacral foramina (posterior sacral foramen) 107. The lateral branches 109 branch out from the sacral nerves 108 (and branch out further along the sacrum as well) and are thought to play a role in the innervation of the SI joint.

Before explaining at least one embodiment of the invention in detail, it is to be understood that the invention is not limited in its application to the details of construction and the arrangement of the components set forth in the following description or illustrated in the drawings. The invention is capable of other embodiments and of being practiced or carried out in various ways. Also, it is to be understood that the phraseology and terminology employed herein is solely for the purpose of description of the illustrated embodiments and should not be regarded as limiting.

With respect to the present invention, one broad method of treating the sacroiliac region of a patient's body by delivering energy may comprise the following steps: inserting at least one probe into the sacroiliac region, the probe comprising at least one energy delivery device; positioning the at least one energy delivery device adjacent material to be treated; and delivering energy through the at least one energy delivery device to create a longitudinal strip lesion; wherein the at least one energy delivery device remains in a static position during creation of the strip lesion. These steps will be discussed in detail in the description of various embodiments below. More specific methods of treating SIJS can be grouped into two categories: those methods that rely on access to at least a portion of the SI joint itself or the immediate vicinity and those that perform a procedure at some other location in the SI region wherein the procedure results in a reduction of SIJS symptoms associated with the SI region (these symptoms may be directly emanating from the SI region or they may have their source in the SI region but be referred to a different region of the body). These two approaches will be presently described in sufficient detail so as to enable one skilled in the art to perform such procedures to treat SIJS.

First Aspect

In accordance with a first aspect of the present invention, a method for the treatment of SIJS by performing a treatment procedure within or adjacent to the SI joint is provided. Some embodiments of this aspect generally comprise the steps of: inserting a device into or adjacent an SI joint in a patient's body and performing a treatment operation in order to treat the SI joint and/or the surrounding region. For example, the method may comprise the steps of: positioning at least one energy delivery device within or adjacent to a sacroiliac joint; and delivering energy through said at least one energy delivery device to create an intra-articular lesion. Energy may be delivered in various configurations and may achieve various results, as will be presently described. This approach is beneficial because it may allow for a treatment procedure that can effectively target neural tissue that derives from both the anterior and posterior (also referred to as ventral and dorsal) primary rami. This approach also reduces the risk of inadvertently damaging crucial neural structures, such as motor nerves or large sensory nerve trunks, since it is designed to affect only the neural structures present within or adjacent the SI joint itself.

More specifically, a first embodiment of the method comprises the steps of: inserting at least one elongated probe into or adjacent the SI joint and delivering energy through the probe(s), wherein the energy may be delivered in order to ablate tissue. Lesioning by ablation can for example be effected using an RF signal having a voltage up to 500V, current up to 5 amps, a frequency of 100 kHz to 10 MHz and an application interval of 5 seconds to 30 minutes; for tissue in the sacroiliac region, the signal may, in some embodiments, have a voltage ranging between 10V and 100V, a frequency of 400-550 kHz, an application interval of 1 to 10 minutes, and a power of 1-20 Watts. In the embodiment shown in FIG. 2A, a probe 120, comprising a distal region 124 and a proximal region (not shown), is inserted into the intra-articular space (also referred to as the joint space) 201 of the SI joint 110. In such an embodiment, probe 120 may comprise an energy delivery device 126 associated with distal region 124, and probe 120 may be operable in a monopolar configuration in conjunction with a grounding pad (not shown) placed at some location on the surface of the patients body. Preferably, probe 120 is capable of creating a strip lesion 230 within SI joint 110, in order to treat as much of the joint as possible within a single treatment procedure. Because the SI joint 110 is difficult to access, the ability to create a strip lesion to treat a large area with the insertion of only one probe is desirable in some situations. For example, a strip lesion having its longest dimension parallel to the longitudinal axis of the energy delivery device may have a length:width and/or length:depth ratio of approximately 3:1, i.e. the length substantially exceeds one or more of the width and/or the depth. Alternatively, another example of a strip lesion is a lesion that has its longest dimension on any axis other than an axis parallel to the longitudinal axis of the energy delivery device. Such a lesion may be created substantially between two or more probes, for example in a bipolar configuration. Alternatively, such a lesion may be created by a single probe. However, the ability to create a strip lesion is not necessary and, in alternate embodiments, the probe may indeed not be required to create or even capable of creating a strip lesion. Rather, various probes, capable of producing lesions of various shapes and sizes, may also be used in conjunction with this method aspect of the present invention and the invention is not limited in this regard.

Referring now to the steps in detail, the step of inserting at least one elongated probe may comprise penetrating into the joint using one or more rigid introducer tubes 116 or other insertional apparatus, and inserting the probe(s) through the introducer(s). Penetration into the joint may also be facilitated by the use of a sharp or pointed probe(s), by the use of a stylet, by the insertion of a guide wire or by any other insertional method or device and the invention is not limited in this regard. It should also be noted that the introducer(s) or other means for insertion may or may not be electrically and/or thermally insulated and they may be curved or straight. In the context of the present invention, the term 'curved' is taken to refer to a deviation from the longitudinal axis of the device. A curved introducer may take several forms and the invention is not limited in this regard. For example, it may be curved along a substantial portion of its radius or it may have a bent tip, wherein the rest of the introducer may be straight. Furthermore, the length and diameter of the introducer are not limited to specific values and any suitably sized introducer may be used. For clarity, the term introducer will be used throughout this specification and is intended to encompass any device that may facilitate entry of the probe into a specific site within the body of a patient. In embodiments that include such devices, these devices may be capable of penetrating into a patient's body as well as penetrating through one or more of the ligaments surrounding the SI joint. In alternate embodiments, the probe may be positioned at the appropriate location within a patient's body without using any additional means to facilitate insertion.

During the step of inserting the probe(s), the position of the probe(s) and/or introducer(s) may be visualized and/or monitored, for example by using fluoroscopy or other imaging modalities. If fluoroscopy is used, visualization may be improved by incorporating radio-opaque markers onto one or more of the probe(s) or introducer(s). In some embodiments, radio-opaque markers may be incorporated onto a distal region of the probe(s) in order to determine the distance that the probes are extending out of the introducer(s). In addition, visual depth markers may be used to help determine the position of the probe(s) or introducer(s) within the body. Furthermore, positioning may be confirmed by measuring the impedance of tissue at the location of the probe(s) or introducer(s), as is known in the art. In some embodiments, positioning may not be verified using these means and a user may rely in whole or in part on his or her knowledge of a patient's anatomy in order to accurately place the device(s).

More specifically, and with reference still to FIG. 2A, introducer 116 may be inserted percutaneously about 1-3 cm below the inferior margin 204 of SI joint 110 and guided anterio-cranially until the tip 118 contacts the ilium about 1 cm above inferior margin 204. Introducer 116 may then be manipulated until a tip of introducer 116 enters the joint space. Probe 120 may then be guided through introducer 116 until a tip of probe 120 enters intra-articular space 201. Probe 120 may then be further advanced to traverse intra-articular space 201 of SI joint 110. Once probe 120 is properly positioned, energy may be applied to create a strip lesion 230 within SI joint 110. In an alternative embodiment and with reference now to FIG. 2B, introducer 116 may be initially manipulated so that the introducer tip 118 is placed just superior to the most posterior point of inferior margin 204. Probe 120 may then be guided through introducer 116 and advanced along the posterior side of the posterior margin 206 of SI joint 110 (outside the joint). Once probe 120 is properly positioned, energy may be applied to create a strip lesion 230 outside and/or within the joint (i.e. the lesion may or may not extend into the intra-articular space 201 of the joint 110). In a further alternative of this treatment procedure, illustrated in FIG. 2C, introducer 116 is manipulated until a tip 118 of introducer 116 enters intra-articular space 201 at the most caudal point of the anterior-inferior margin 208 of SI joint 110. Probe 120 may then be guided through introducer 116 and along the posterior side of the anterior margin 209 of SI joint 110 (inside the joint). Once probe 120 is properly positioned, energy may be applied to create a strip lesion 230 along the anterior side of SI joint 110. In any of these embodiments, the introducer 116 may be inserted some distance into the SI joint 110.

Referring now to the step of delivering energy through the probe(s), this may be accomplished by providing, for example, a generator, operable to deliver radiofrequency (RF) energy in the range of for example about 100 kHz to about 1 GHz, connecting the generator to the probe(s) and operating the generator to deliver said RF energy to the SI joint through an energy delivery device associated with a distal region of the probe(s). A generator that may be used to perform these treatment methods, by way of non-limiting example, is the Pain Management Generator (PMG) from Baylis Medical Company Inc., Montreal, QC, Canada. Features of this generator are described in co-pending U.S. patent application Ser. No. 10/122,413, filed on Apr. 16, 2002; Ser. No. 10/323,672, filed on Dec. 20, 2002; Ser. No. 10/864,410, filed on Jun. 10, 2004; Ser. No. 10/893,274, filed on Jul. 19, 2004; and Ser. No. 11/198,099, filed on Aug. 5, 2005. All of the aforementioned applications are incorporated herein by reference. In one embodiment, the generator is operable to deliver sufficient energy to the target tissue through the probe(s) so that tissue within or adjacent to the SI joint may be ablated, as has been defined earlier. In such embodiments that involve the ablation of a region of tissue, the tissue ablated according to this aspect of the invention can include, but is not limited to, one or more of: neural tissue, whose ablation can prevent the transmission of pain sensation; structural or connective tissue, whose ablation can cause a contraction of collagen and a reduction in the volume of the intra-articular space of the joint; and vascular tissue, whose ablation may result in the disruption of nutrient supply to one or more neural structures. In alternate embodiments, the energy delivered by the generator through the probe(s) may not ablate tissue but may perform one or more other treatment functions, such as altering the structure of collagen (without causing cellular coagulation) or globally heating the joint, thereby altering the function of neural tissue, without necessarily ablating or destroying the nerves themselves. Thus, the function of neural tissue may be altered with or without ablating the neural tissue. Other alternative treatment functions may include, but are not limited to, denaturing enzymes or increasing heat shock proteins in the SI joint. Alternatively, RF (or other) energy could be delivered in a series of amplitude or frequency modulated pulses, whereby tissue heating is inhibited by interrupting periods of energy delivery with relatively long periods in which no energy is delivered. By pulsing the energy in this manner, a voltage that is sufficiently high to affect a prolonged disruption of the function of neural tissue may be used, while maintaining the tissue at a temperature such that no lesion will form, or such that the formation of a lesion will be inhibited. In further embodiments, a generator may not be used. In these embodiments, energy may be generated by a battery or any other means (in which case the entire system [probe and energy source] may be hand-held/portable/modular) and the invention is not limited in this regard. Without limitation, any delivery of energy that may result in a treatment effect to alleviate symptoms of SIJS is intended to be included within the scope of this aspect of the present invention.

Regarding connecting the generator to the probe(s), the generator may, in some embodiments, be releasably coupled to the probe(s). For example, this may be achieved by providing releasable electrical connectors at or close to the proximal region of the probe(s). In embodiments in which the probe(s) are cooled, the proximal region of the probe(s) may further comprise releasable connectors, such as Luer locks, to couple one or more means for cooling, such as peristaltic pumps and associated tubing, to the probe(s). In alternate embodiments, the probe(s) may be permanently attached to the generator and/or the one or more means for cooling.

As mentioned above, in some embodiments, the probe(s) may be operable to create a single strip lesion within the joint. In addition, the probe(s) may be operable to create such a lesion during the course of a single energy delivery step, without the need for one or more of removal of the probe(s), reinsertion of the probe(s) or intentional repositioning of the probe(s). In other words, the probe may remain in a substantially static position during the creation of the strip lesion. It should be noted, however, that creating strip lesions through one or more probe repositioning or energy delivery steps, as well as creating individual, non-strip lesions, also fall within the scope of this invention. In addition, although the aforementioned embodiments have been described using only one probe, several probes may be used in order to deliver energy within the SI joint. Furthermore, each of these probes may comprise one or more energy delivery devices and the invention is not limited in this regard. For example, in alternate embodiments, two or more probes may be used in a bipolar configuration. In some such embodiments, the probes may be spaced apart by a distance that is not greater than about five times the diameter of the energy delivery devices located on the probes. Such a spacing may be advantageous when using non-cooled probes. Using cooled probes, as discussed below, may allow for a larger separation distance between the probes. In addition, in some embodiments, the probes may be separated by a distance of at least about 1 cm. In other embodiments, probe separation may vary and may be more or less than the aforementioned maximum and minimum distances. In yet further embodiments, three or more probes may be used in a triphasic configuration. It should be noted that when more than one probe is used, the probes may be operated in a monopolar configuration and the invention is not limited in this regard. For example, several probes may be operated in a monopolar configuration, whereby a specific lesion shape may be obtained by determining an optimal spacing between probes that may produce a specific interference pattern and thus, a specific current density resulting in a desired lesion shape.

In some embodiments of this aspect of the present invention, the method may further comprise a step of moving the probe(s) to another location within the tissue if the user so desires. The probe(s) may be moved before, during, or after the step of delivering energy, and may be moved one or more times. The step of moving the probes may comprise one or more of the following actions: applying a force to bend the probe within the tissue (wherein the probe may thus be described as a 'steerable' probe), moving the probe intact within the tissue, removing the probe intact from the tissue, re-inserting the probe into the tissue and moving one or more parts of the probe (for example, extending or retracting a segmented probe telescopically) to move the position of one or more functional elements within the tissue.

In use, and with reference again to FIGS. 2A to 2C, a first embodiment of this aspect of a method of the present invention may be practiced as follows: a patient is made to lie prone on an operating table or similar structure, a grounding pad is placed on the surface of the patient's body and local anesthetic is provided in the area to be treated (for example, at or near the SI joint). If neural stimulation will be performed, as discussed below, the stimulation step may be performed prior to the delivery of anesthetic (if anesthetic is used). Prior to the insertion of the probe(s) or introducer(s), fluoroscopic imaging or other means may be used to visualize a patient's sacroiliac region in order to ascertain the desired approach for inserting the device(s) into the SI joint. This is particularly important with respect to SIJS treatment procedures because the anatomical structures involved may vary significantly from patient to patient. Various angles of approach and sites of entry may be used and the invention is not limited in this regard. After introducer 116 has been inserted, the position of introducer 116 may be verified using fluoroscopic imaging (or other imaging modalities) or other means, after which probe 120 may be inserted through a bore or lumen of introducer 116 such that at least a portion of distal region 124 of probe 120 is located within or adjacent to joint 110, depending on the specific target lesion site. It should be noted that, in those embodiments that comprise a stylet to facilitate positioning of the probe, the stylet may be located within an introducer and may be removed from the introducer prior to insertion of the probe.

Figure 2A:
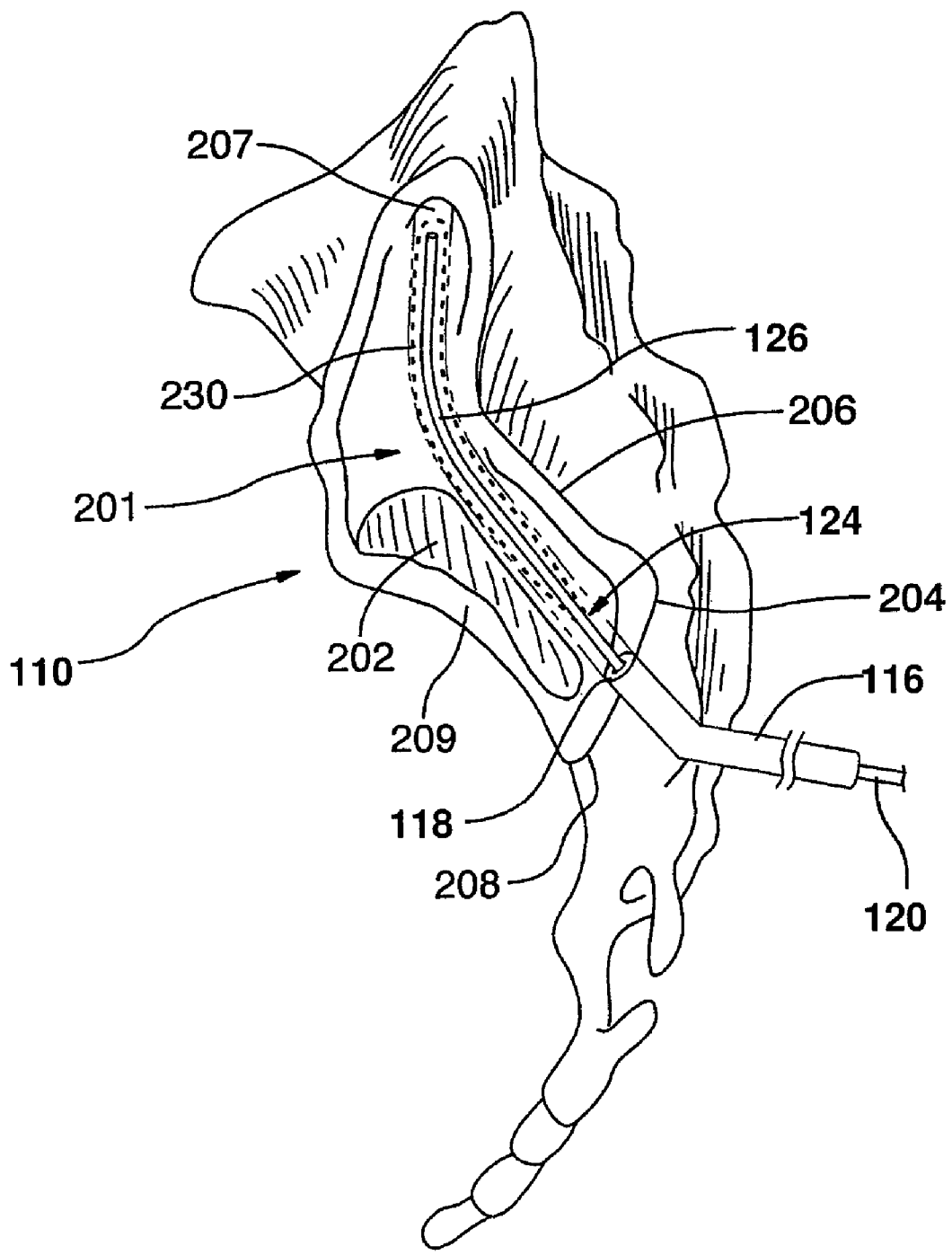
FIGS. 2A, 2B and 2C are cross-sections through a typical sacroiliac joint of a patient showing the position of a probe in alternate embodiments of the present invention.
Figure 2B:
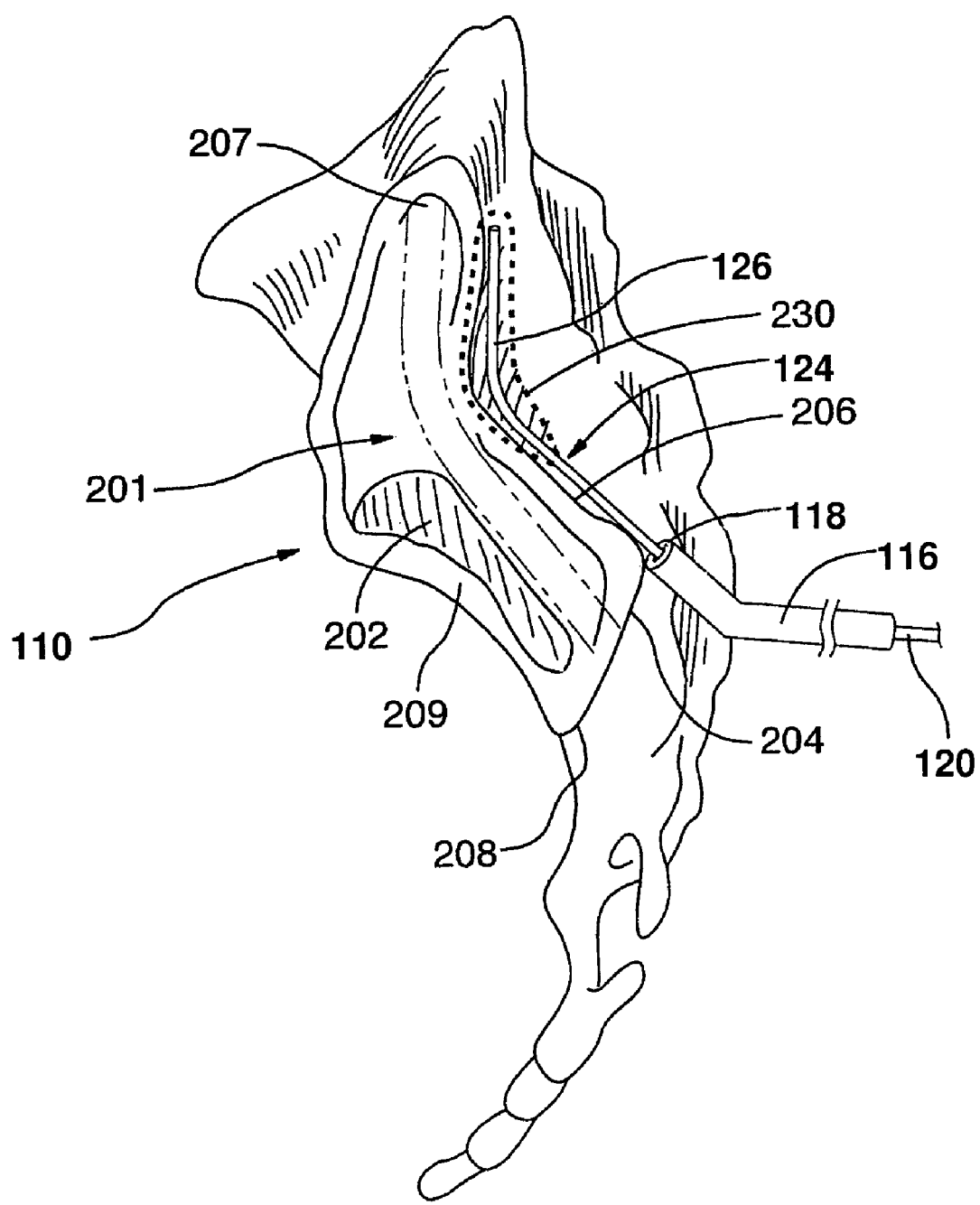
Figure 2C:
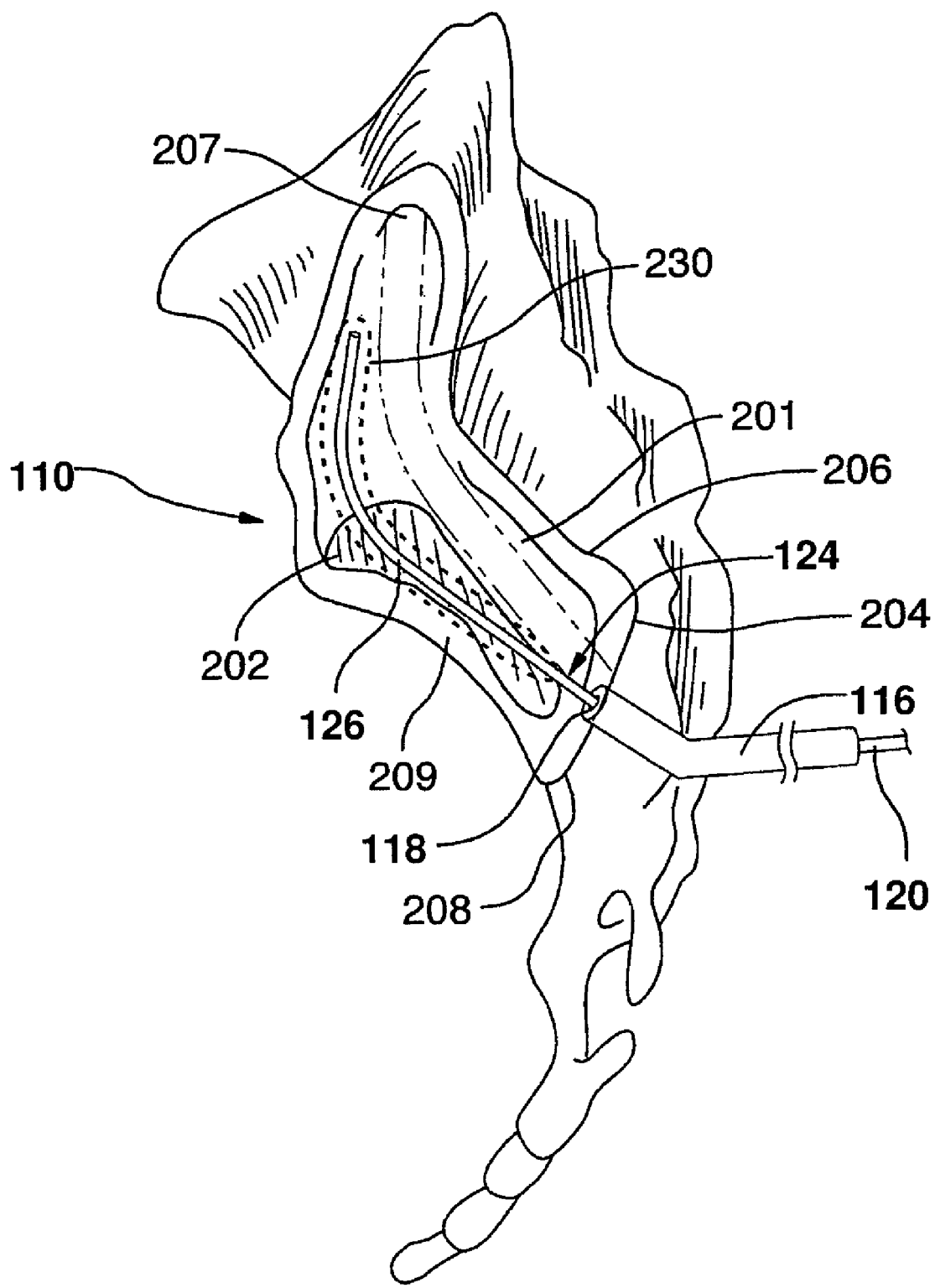

In some embodiments, as shown in FIG. 2A, probe 120 is advanced far enough into joint 110 so that a strip lesion 230 will be created across a substantial part of the long axis of joint 110 when energy is delivered to energy delivery device 126. Probe 120 may be advanced until further advancement is impeded by an anatomical structure, such as a bone or a ligament. It may be desirable that probe 120 be inserted into joint 110 in such a way so as to minimize damage to the connective tissues of the joint, including the articular cartilage located at the surfaces of the bones, as well as the various ligaments associated with joint 110. Therefore, in order to avoid damaging these tissues, the probe may be inserted into the cartilaginous space 207 of joint 110, as shown in FIG. 2A, in which case it would be desirable to have a probe flexible enough to conform to the boundaries of cartilaginous space 207. In addition, some embodiments may utilize a probe capable of creating a relatively thin strip lesion (i.e. a strip lesion with a small diameter or a strip lesion with short minor axes) so that the lesion does not extend too deeply into the cartilage. Depending on the specific probe that is used, a user may receive tactile feedback to indicate that the probe is contacting cartilage or ligamentous tissue and the user may then decide to retract the probe slightly and attempt to reposition the probe. In alternate embodiments, a probe may be introduced into the SI joint without being inserted into the cartilaginous space, for example in order to reach certain nerves which may be located throughout the joint, for example as shown in FIG. 2B. In general, when inserting probe 120 into joint 110, care should be taken to insert the probe as far as possible into joint 110 while minimizing the collateral damage to the tissues that make up the joint. In other embodiments, the probe may not initially extend a large distance into the joint, in which case smaller lesions may be made while advancing the probe slowly through the joint space in order to treat as much of the joint space as possible. In yet further embodiments, it may be desirable to have at least a portion of the probe located proximate to or within a region of cartilage. For example, this may be desirable if it is suspected that a fissure or other defect exists within the cartilage, in which case it may be beneficial to apply energy directly to the cartilage in order to heal the fissure or other defect.

At this point, energy may be delivered from a generator via energy delivery device 126 to tissue of SI joint 110. If the probe is steerable, the probe tip may be maneuvered into a second location within the joint and energy may again be delivered to ablate the neural tissue at the second location. This may be repeated as many times as the user wishes. If the probe is not steerable, the probe may be removed from the joint and/or the patient and the positioning and insertion steps may be repeated so that the probe is located at a second position, at which point energy may be delivered again at this location. Once the user has determined that enough neural tissue has been ablated or otherwise affected, the introducer and probe may be removed from the body and the patient should be allowed to recover. It should be noted that this description is intended to be exemplary only and that other embodiments are envisioned as well. In addition, this invention is not intended to be limited by the number and type of probes used in this and other embodiments as well as the number and type of lesions created by these probes. It is also important to note that the aforementioned embodiments have been described with reference to a typical structure of an SI joint, as can be found in the literature. However, the SI joint is known to be extremely variable and the structures discussed with respect to this preferred embodiment may not be present in some individuals or may be located in different areas of the joint. Thus, the present invention is not intended to be limited by these embodiments.

In alternate embodiments of this aspect of the present invention, energy may be delivered in forms other than radiofrequency electrical energy, including but not limited to: other forms of electromagnetic energy, for example microwave energy or optical energy; thermal energy; mechanical energy; and ultrasonic energy; and combinations thereof. Additionally, the step of delivering energy could involve the use of other energy delivery devices including, but not limited to: microwave probes, optical fibers, resistive heaters, and ultrasound emitters.

The step of delivering energy to the tissue, may involve, in some embodiments, the use of devices in which the one or more probes are actively or passively cooled. Cooling of probes can prevent the searing or coagulation of tissue directly adjacent to the probe(s) and can prevent the vaporization of liquid within the tissue. Cooling can also be used to increase the maximum lesion volume that can be formed in a given tissue.

In addition to optionally measuring impedance, as in one embodiment described above, some embodiments further comprise an additional step of measuring the temperature of tissue at least at one location. This is generally desirable so as to ensure that a given region of tissue is not exceeding a certain temperature. For example, in some embodiments it may be desirable to maintain the temperature of tissue at or below a temperature required for neural ablation. A means for monitoring temperature may be located on or within or about a distal region of the one or more probes and the temperature of tissue located proximate to the distal region(s) of the probe(s) may be monitored using the means for monitoring temperature. Alternatively or in addition, a means for monitoring temperature may be located at a different location on the one or more probe(s) to monitor the temperature of a region of tissue located some distance away from the distal region(s) of the probe(s). Furthermore, one or more separate means for monitoring temperature may be inserted into the patient's body in order to monitor the temperature of one or more specific regions of tissue. The means for monitoring temperature may take the form of one or more thermocouples, thermistors, optical thermal sensors or any other means for monitoring or sensing temperature and the invention is not limited in this regard. The means for monitoring temperature may be connected directly to the energy source (e.g. the RF generator) or they may be monitored by an independent temperature monitoring device. These embodiments are intended to be exemplary only and are not intended to limit the present invention in any way.

As a feature of this aspect of the present invention, an embodiment of this method may further comprise one or more steps of modifying a treatment procedure in response to one or more measured parameters. These measured parameters may include, but are not limited to, temperature, position of the probe(s) or impedance. For example, if a temperature measurement is determined to be outside of a desired range, a treatment procedure may be modified by, for example, altering the amount of energy delivered by the generator (for example, by altering the maximum allowable temperature or changing the temperature ramp rate), modifying or modulating the one or more means for cooling in some way (for example, by adjusting the rate of coolant flow), or terminating the procedure. As another example, the amount of energy delivered by the generator may be modified based on the position of the one or more probes (for example, depending on the distance between a probe and the target treatment site or on the distance between the probes themselves when more than one probe is used). In such embodiments, a feedback system may be incorporated directly into the energy source so that any modification of a treatment procedure in response to a measured parameter may occur automatically.

In other embodiments, there may not be an automatic feedback system in place, in which case a user may manually modify a treatment procedure in response to a measured parameter. In addition to modifying a treatment procedure based on measured parameters, this invention also provides for a step of determining the initial parameters to be used in a treatment procedure (for example, the initial maximum power level or tissue temperature, temperature ramp rate, etc.) using information that is known about the particular SI joint to be treated. For example, if pre-treatment testing reveals specific information about the SI joint of a particular patient (this information may include, but is not limited to: joint geometry, presence or absence of synovial fluid, etc.), that information may be used to decide on what parameters to use initially for the treatment procedure.

In some embodiments of this aspect of the present invention, the step of performing a treatment, for example in order to reduce pain associated with SIJS, may comprise the addition or removal of material to or from the joint. Material that may be added to the joint includes, but is not limited to: alcohol, chemical lysing agents, pharmaceutical agents (including, but not limited to, anesthetics and other medicaments), sealants, matrix molecules such as collagen or fibrinogen, electrolyte solutions, contrast media, or any combination of the above. Material that may be removed from the joint includes, but is not limited to: synovial fluid, ligamentous tissue, cartilage and any other material whose removal may help to treat the SI joint. The removal of material may be accomplished through various means, which can include aspiration, vaporization or mechanical conveyance. Furthermore, the steps of addition and removal of material can be performed concurrently, for example by irrigating the joint with a liquid medium while aspirating the liquid effluent from the space. The addition or removal of material may also be combined with the delivery of energy, as has described above, wherein the delivery of energy and the addition or removal of material may occur concurrently or sequentially. An exemplary device for removing material from a patient's body has been described in co-pending U.S. patent application Ser. No. 11/128,342, filed on May 13, 2005 as well as U.S. provisional patent application 60/594,109 filed on Mar. 11, 2005. These applications are herein incorporated by reference.

According to this aspect of the present invention, as has been described, one or more probes or other devices are placed at some location within or adjacent to the SI joint. It should be understood that the probe(s) may be inserted into any tissue within or adjacent to the joint, including, but not limited to the ligaments, cartilage or intra-articular region of the joint. Furthermore, as has already been mentioned, a probe may be inserted using any approach that allows access to the joint, including but not limited to: a superior posterior approach, an inferior posterior approach, or an anterior approach. For example, in one alternate embodiment, a probe may be inserted percutaneously using an inferior posterior approach and advanced into the SI joint through a synovial capsule 202 located at or proximate to inferior joint margin 204. In such embodiments, the probe may be operable to conform to the shape of synovial capsule 202. In yet another embodiment, a probe and/or introducer may be inserted into a patient's body in such a manner so that the probe and/or introducer can be positioned proximate to the posterior margin of the SI joint, with the probe oriented approximately perpendicularly to the patient's body. In such an embodiment, the probe may be inserted into the joint and used to create an elongate strip lesion along an anterior-posterior plane through the joint. Thus, this invention is not limited to one specific approach.

If more than one probe is used, the probes may be inserted into the joint using different approaches. For example, when practicing this method aspect of the present invention using two probes in a bipolar configuration, as has been previously mentioned, the probes may be inserted at a relatively higher angle (i.e. closer to an anterior-posterior plane approach) with respect to the patient's body. In such embodiments, the probes may not penetrate as far into the SI joint and may be more effective in treating the periphery of the SI joint, for example along the posterior joint line. In addition, when using probes in a bipolar configuration in this manner, it may be useful to follow a 'leapfrog' approach, wherein the two probes are inserted to initial locations and a lesion is created between the probes. Once the first lesion is created, the first probe is repositioned so as to be located on the other side of the second probe, for example more cephalad (towards the head, i.e. superior) in the joint, and a second lesion is created. Following this, the second probe is repositioned so as to be located on the other side of the first probe, even more cephalad in the joint, and so on. This procedure is repeated along the long axis of the joint until a sufficient portion of the joint has been treated. Depending on the specific case, this may occur after as few as one or two lesions are created or it may require treating the entire posterior margin of the joint, including in the area of the crest of the ilium. This method can also be practiced by using a multiplicity of probes and leaving each probe in place. In other words, once a probe is in place it may remain there and further probes may be inserted in order to achieve this 'leapfrog' lesioning approach. In this way, an effective strip lesion may be created. In other embodiments, bipolar probes may be used in conjunction with various other approaches and this invention is not limited to using bipolar probes with this specific approach.

In embodiments of the present invention that employ more than one probe, the probes used during the course of a treatment procedure may form part of the circuit of an electrical impedance meter, as is known in the art, wherein energy may be transmitted between the probes through a region of tissue, allowing a user to determine the impedance of said region of tissue. This feature may be useful to determine whether or not the impedance of the tissue lies within a 'normal' range—if the impedance of the tissue is found to be outside that range, it may be indicative of an injury or defect within the tissue. As mentioned above, a single probe may also have an impedance measuring capability, for example to help determine the location of the probe within a patient's body.

As an additional feature of this aspect of the present invention, certain embodiments may further comprise a step of performing a function to map the neural pathways in the tissue and this step may occur one or more times throughout the course of the procedure. The step of performing a function to map the neural pathways in the tissue can involve, in some embodiments, stimulation of the neural tissue at one or more physiological stimulation frequencies and subsequent observation to determine the effect of said stimulation. Various frequencies (for example, between about 1 and about 100 Hz) and voltages (for example, between 0.1 and 5 Volts) can be used to stimulate both sensory and motor nerves. Observation of said stimulation can take the form of visual, sensory, mechanical, or electrical detection of muscle activity, or the form of sensory or electrical detection of nociceptive or other sensory neural activity (e.g. temperature sensation). Using this step, it can be determined whether a target nerve or group of nerves has a function that would contraindicate its ablation or functional alteration. In some embodiments, the lack of a contraindication would lead to the step of delivering energy, whereas the presence of a contraindication would lead back to the step of inserting a probe or probes, whereby the step of inserting a probe or probes includes modifying the position of a probe or probes within the body. Furthermore, in some embodiments, a method of this aspect of the present invention may comprise a step of stimulating neural tissue after a treatment procedure in order to determine the effectiveness of the treatment procedure.

Second Aspect

In accordance with a second aspect of the present invention, a method for the treatment of SIJS by performing a treatment procedure outside of the SI joint is provided. The method generally comprises the steps of inserting a device into a region of tissue external to the SI joint in a patient's body and performing a treatment operation in order to reduce one or more symptoms associated with SIJS. For example, a treatment procedure of this method aspect may be performed proximate to a patient's sacral region, within one or more of the SI ligaments or in a region of tissue adjacent to one or more nerves that innervate the SI joint. These locations are exemplary only and are not intended to limit the present invention in any way. The scope of this aspect of the present invention is intended to cover any treatment procedures performed external to the SI joint that fall within the limitations of the appended claims. This approach is beneficial because it may allow for a treatment procedure that can effectively target neural tissue that innervates the SI joint without having to actually enter the joint itself. Furthermore, if a patient's pain is emanating from the SI joint ligaments, it may be beneficial to target the neural tissue before it reaches the ligaments in order to alleviate this pain. In addition, energy may be delivered to connective tissue in the SI region (such as, for example, one of the sacroiliac ligaments) in order to, for example, tighten or loosen the tissue. Generally, it may be beneficial to treat neural tissue as close to the nerve root as possible, in order to increase the effectiveness of the treatment procedure.

Similar to what has been discussed with respect to the first aspect of the present invention, a first embodiment of the second aspect generally comprises the steps of inserting one or more probes into a region of tissue in a patient's body and delivering energy through the probe(s) in order to relieve symptoms of SIJS, wherein the energy may be delivered, for example, in order to ablate tissue. In the embodiment shown in FIG. 1, a probe 120, comprising a distal region 124 and a proximal region (not shown), is inserted proximate to sacrum 100. In this embodiment, probe 120 comprises an energy delivery device 126 associated with distal region 124, and probe 120 may be operable in a monopolar configuration in conjunction with a grounding pad (not shown) placed at some location on the surface of the patient's body. Probe 120 may be capable of creating a strip lesion 130 adjacent sacrum 100, in order to treat as many neural structures of the dorsal sacral plexus as possible within a single treatment procedure. However, the ability to create a strip lesion is not necessary in some embodiments. Rather, various probes, capable of producing lesions of various shapes and sizes, may also be used in conjunction with this aspect of the present invention and the invention is not limited in this regard.

Referring now to the steps in detail, the step of inserting a device into a region of tissue may comprise penetrating into the tissue using one or more rigid introducer tubes or other insertional apparatus, and inserting the probe(s) through the introducer(s). Penetration into the tissue may also be facilitated by the use of a sharp or pointed probe(s), by the use of a stylet, by the insertion of a guide wire or by any other insertional method or device and the invention is not limited in this regard. It should also be noted that the introducer(s) or other means for insertion may or may not be electrically and/or thermally insulated and they may be curved or straight. Furthermore, the length and diameter of the introducer are not limited to specific values and any suitably sized introducer may be used. As noted above, the term introducer is used throughout this specification and is intended to encompass any device that may facilitate entry of the probe into a specific site within the body of a patient. In such embodiments, these devices may be capable of penetrating into a patient's body as well as penetrating through one or more of the ligaments of the sacroiliac region. In alternate embodiments, the probe may be positioned at the appropriate location within a patient's body without using any additional means to facilitate insertion.

In some embodiments of the present invention, a supporting or stabilizing apparatus or device may be used to help prevent inadvertent movement of the probe(s) and/or introducer(s). For example, the supporting or stabilizing apparatus (i.e. a means for supporting or stabilizing) may, for example, take the form of a frame for fixing the probe(s) and/or introducer(s) in a desired position. During the step of inserting the probe(s), the position of the probe(s) or introducer(s) may be visualized and/or monitored, for example by using fluoroscopy or other imaging modalities. If fluoroscopy is used, visualization may be improved by incorporating radio-opaque markers onto one or more of the probe(s) or introducer(s). In some embodiments, radio-opaque markers may be incorporated onto a distal region of the probe(s) in order to determine the distance that the probes are extending out of the introducer(s). In addition, visual depth markers may be used to help determine the position of the probe(s) or introducer(s) within the body. Furthermore, positioning may be confirmed by measuring the impedance of tissue at the location of the probe(s) or introducer(s), as is known in the art. In some embodiments, positioning may not be verified using these means and a user may rely in whole or in part on his knowledge of a patient's anatomy in order to accurately place the device(s).

Referring now to the step of delivering energy through the probe(s), this may be accomplished for example by providing a generator, operable to deliver radiofrequency (RF) energy, connecting the generator to the probe(s) and operating the generator to deliver said RF energy to the tissue through the energy delivery device associated with, for example, a distal region of the probe(s). In certain embodiments, the generator is operable to deliver sufficient energy to the tissue through the probe(s) so that the tissue may be ablated, as has been defined earlier. In such embodiments that involve the ablation of a region of tissue, the tissue ablated according to this method aspect of the invention can include, but is not limited to, neural tissue, whose ablation can prevent the transmission of pain sensation and vascular tissue, whose ablation may result in the disruption of nutrient supply to one or more neural structures. In alternate embodiments, the energy delivered by the generator through the probe(s) may not ablate tissue but may perform one or more other treatment functions such as altering the structure of collagen (without causing cellular coagulation). Alternatively, RF (or other) energy could be delivered in a series of amplitude or frequency modulated pulses, whereby tissue heating is inhibited by interrupting periods of energy delivery with relatively long periods in which no energy is delivered. By pulsing the energy in this manner, a voltage that is sufficiently high to affect a prolonged disruption of the function of neural tissue may be used, while maintaining the tissue at a temperature such that no lesion will form, or such that the formation of a lesion will be inhibited. In further embodiments, a generator may not be used. In these embodiments, energy may be generated by a battery (in which case the entire system [probe and energy source] may be hand-held/portable/modular) or any other means and the invention is not limited in this regard. Any delivery of energy that may result in a treatment effect to alleviate one or more symptoms of SIJS is intended to be included within the scope of this aspect of the present invention.

Regarding connecting the generator to the probe(s), the generator may, in some embodiments, be releasably coupled to the probe(s). For example, this may be achieved by providing releasable electrical connectors at or proximate to the proximal region of the probe(s). In embodiments in which the probe(s) are cooled, the proximal region of the probe(s) may further comprise releasable connectors, such as Luer locks, to couple one or more means for cooling, such as peristaltic pumps and associated tubing, to the probe(s). In alternate embodiments, the probe(s) may be permanently attached to the generator and/or the one or more means for cooling.

In some embodiments, the probe(s) used in this method aspect of the present invention may be operable to treat a plurality of neural structures without the need for one or more of removal of the probe(s), reinsertion of the probe(s) or repositioning of the probe(s). For example, at least two branches of the sacral nerves 108 may be treated. These two branches may comprise two or more branches of the same sacral nerve, as shown, for example, in FIGS. 3A and 3B. Alternatively, these two branches may comprise at least one lateral branch 109 from one sacral nerve and at least one lateral branch from a different sacral nerve, as shown, for example, in FIG. 1. One way of achieving this effect is to create a single strip lesion at a desired location, wherein said single strip lesion may be of sufficient size so as to affect multiple neural structures. As has been mentioned, the probe(s) may be operable to create such a lesion during the course of a single energy delivery step, i.e. without the need for one or more of removal of the probe(s), reinsertion of the probe(s) or repositioning of the probe(s). It should be noted, however, that creating strip lesions through one or more probe repositioning steps, as well as creating individual, non-strip lesions, on one or more neural structures or other bodily material, also falls within the scope of this aspect of the present invention.

In addition, this aspect of the present invention is not limited to using only one probe and several probes may be used with this treatment method. Furthermore, each of these probes may comprise one or more energy delivery devices and the invention is not limited in this regard. For example, in alternate embodiments, two or more probes may be used in a bipolar configuration. In such embodiments, the probes may be spaced apart by a distance that is not greater than five times the diameter of the energy delivery device located on the probes. In other embodiments, probe separation may vary and may be more or less than the aforementioned maximum and minimum distances. In yet further embodiments, three or more probes may be used in a triphasic configuration.

As a feature of this aspect of the present invention, some embodiments may further comprise a step of moving the probe(s) to another location within the tissue if the user so desires. The probe(s) may be moved before, during, or after the step of delivering energy, and may be moved one or more times. The step of moving the probes may comprise one or more of the following actions: applying a force to bend the probe within the tissue (wherein the probe may thus be described as a 'steerable' probe), moving the probe intact within the tissue, removing the probe intact from the tissue, reinserting the probe into the tissue and moving one or more parts of the probe (for example, extending or retracting a segmented probe telescopically) to move the position of one or more functional elements within the tissue.

Thus, in one embodiment of this aspect of the present invention, and with reference again to FIG. 1, a method for treating SIJS may be practiced as follows: a patient is made to lie prone on an operating table or similar structure, a grounding pad is placed on the surface of the patient's body and local anesthetic is provided. Prior to the insertion of the probe(s) or introducer(s), fluoroscopic imaging or other means may be used to visualize a patient's sacroiliac region in order to ascertain the desired approach for inserting the device(s) into the desired tissue. This is particularly important with respect to SIJS treatment procedures because the anatomical structures involved may vary significantly from patient to patient. In one embodiment, a probe 120, operating in a monopolar configuration, would be positioned in proximity to the posterior sacral foramina 107, such that the step of delivering energy will result in an alteration of the function of the neural tissue of the dorsal sacral plexus. Therefore, in this embodiment, an introducer 116 may be inserted into a patient's body from a generally inferior-posterior approach under fluoroscopic guidance, such that a distal end 118 of introducer 116 is positioned proximate to or adjacent the inferior margin 101 of sacrum 100. For example, in some embodiments, a substantially cranial-caudal or caudal-cranial approach may be utilized, wherein introducer 116 and/or probe 120 are inserted substantially along the cranial-caudal/inferior-superior axis of the patient's body, which allows for a relatively straightforward insertion procedure. It should be noted that, in the context of these embodiments, an approach substantially along the cranial-caudal axis is not intended to refer to an insertion along precisely this axis of the patient's body. Rather, there may be some lateral/medial and/or anterior/posterior components to the approach vector as long as the approach to the sacrum is not impeded by anatomical obstacles, such as the iliac crest, that may have to be negotiated. In other words, this approach is intended to allow for a fairly straightforward insertion into the target site. In alternate embodiments, other approaches, such as, for example, a more lateral approach may be used, depending on the user's preference.

Figure 3A:
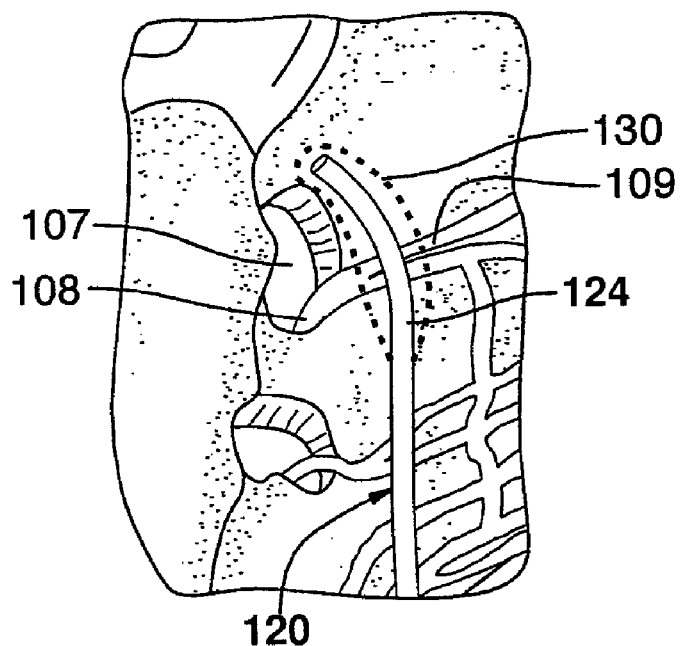
FIGS. 3A and 3B are illustrations of a posterior sacral foramina, showing the position of a probe in further embodiments of the present invention.
Figure 3B:
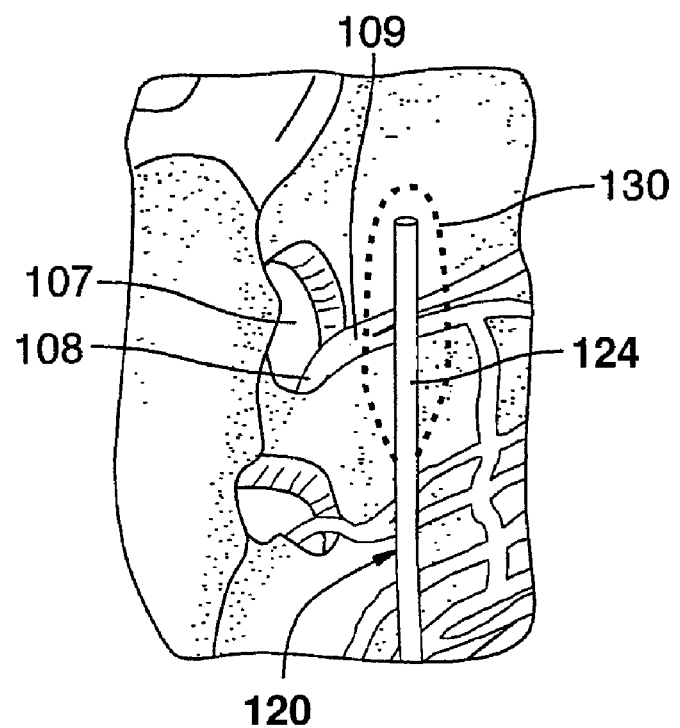

In some embodiments, distal end 118 of introducer 116 is positioned immediately adjacent to the bone, without any ligaments or other connective tissue in between distal end 118 and sacrum 100. In other embodiments, various angles of approach and sites of entry may be used. Depending on the site of entry and the angle of approach that are chosen, the introducer may be either curved or straight. A curved introducer may take several forms and the invention is not limited in this regard. For example, it may be curved along a substantial portion of its radius or it may have a bent tip, wherein the rest of the introducer may be straight. In addition, the distal region 124 of probe 120 may be curved or straight, as shown in FIGS. 3A and 3B.

At this point, and with reference again to FIG. 1, the position of introducer 116 may be verified using fluoroscopic imaging (or other imaging modalities) or other means, after which probe 120 may be inserted through a bore or lumen of introducer 116 such that at least a portion of distal region 124 of probe 120 is located adjacent to and along sacrum 100. It should be noted that, in those embodiments that comprise a stylet to facilitate positioning of the probe, the stylet may be located within an introducer and may be removed from the introducer prior to insertion of the probe. As shown in FIG. 1, probe 120 may be advanced to the extent that elongate strip lesion 130 will be created around probe 120 across a substantial part of the dorsal sacral plexus when energy is delivered to energy delivery device 126. In this embodiment, it may be beneficial to use a flexible probe which is capable of conforming to the surface of sacrum 100. In other embodiments, the probe may extend various distances outside of the introducer and the invention is not limited in this regard. For example, if using a brush electrode comprising a plurality of electrically conductive filamentary members, an effective strip lesion may be created by dragging the probe along a tissue while supplying energy to the filaments, analogous to painting with a paint brush. In such an embodiment, the probe may be extended from the introducer such that a distal end of the probe may be located adjacent to the SI sacral nerve of the sacral posterior rami, so that, when the probe is retracted back into the introducer, a lesion will be created covering all of the nerves between the SI level and the location of the introducer.

It is advisable, at this stage, to ascertain the location of probe 120 with respect to any sensory and/or motor nerves that may be located nearby by stimulating the neural tissue at one or more physiological stimulation frequencies and determining the effect of said stimulation, as will be described in more detail below. Using this step, it can be determined whether a target nerve or group of nerves has a function that would contraindicate its ablation or functional alteration. In some embodiments, the lack of a contraindication would lead to the step of delivering energy, whereas the presence of a contraindication would lead back to the step of inserting a probe or probes, whereby the step of inserting a probe or probes comprises modifying the position of a probe or probes within the body. In alternate embodiments, no stimulation is performed and a user may rely on his or her knowledge (for example, of the patient's anatomy) to determine whether or not to proceed with the treatment procedure.

At this point, energy may be delivered from the generator (not shown) via energy delivery device 126 to the region of tissue located proximate to energy delivery device 126. If the probe is steerable, the probe tip may be maneuvered into a second location and energy may again be delivered to ablate the neural tissue at the second location. This may be repeated as many times as the user feels is necessary. If the probe is not steerable, the insertion and positioning steps may be repeated so that the probe is located at a second position, at which point energy may be delivered again at this location. Once the user has determined that enough neural tissue has been ablated or otherwise affected, the introducer and probe may be removed from the body and the patient should be allowed to recover. It should be noted that this description is intended to be exemplary only and that other embodiments are envisioned as well. In addition, this invention is not intended to be limited by the number and type of probes used in this and other embodiments as well as the number and type of lesions created by these probes.

Relief of SIJS symptoms may result from the fact that the neural tissue that may be affected by this procedure innervates the Si joint and thus, by treating the neural tissue external to the joint, pain transmission from the joint itself may be indirectly affected. As has been described, treatment of the neural tissue may be accomplished by the delivery of RF energy supplied to the probe(s) by a generator. Each probe may be furnished with one or more electrodes, and one or more probes may be used. If two or more electrodes are used, the electrodes may be in a monopolar, bipolar, multipolar, or multiphasic configuration. For example, several probes may be operated in a monopolar configuration, whereby a specific lesion shape may be obtained by determining an optimal spacing between probes that may produce a specific interference pattern and thus, a specific current density resulting in a desired lesion shape. Energy may be delivered to ablate at least a portion of the neural tissue of the dorsal sacral plexus, in order to reduce pain associated with the SI region. Alternatively, energy may be delivered in order to alter the function of the neural tissue of the dorsal sacral plexus, without damaging the neural tissue, for example by delivering energy in a series of amplitude or frequency modulated pulses, as described above. Furthermore, as was mentioned above, energy may be delivered in order to perform some other treatment function that may result in relief of symptoms due to SIJS. For example, energy may be delivered to one or more of the sacroiliac ligaments in order to repair some defect in the ligaments or to tighten or loosen the ligaments. In addition, applying a treatment procedure (other than or in addition to neural ablation) external to the joint, for example, by heating one or more sacroiliac ligaments, may indirectly treat the joint itself as well (for example, by causing the shrinkage of collagen within the joint due to heat conduction from the ligaments).

In some embodiments, the steps of inserting one or more probes into a region of tissue in a patient's body and delivering energy through the probe(s), can be repeated one or more times, for example at each of the posterior sacral foramina as well as around the lower lumbar vertebrae. In other words, the steps described above may be used to alter the function of neural tissue around each of the posterior sacral foramina as well as the lower lumber vertebrae. In other embodiments, the probe(s) may be inserted using an anterior approach, in which case the treatment procedure may involve the alteration of the function of neural tissue adjacent the anterior or posterior sacral foramina.

In alternate embodiments of this aspect of the present invention, energy may be delivered in forms other than radiofrequency electrical energy, including but not limited to: other forms of electromagnetic energy, for example microwave energy or optical energy; thermal energy; mechanical energy; and ultrasonic energy; and combinations thereof. Additionally, the step of delivering energy could involve the use of other energy delivery devices including, but not limited to: microwave probes, optical fibers, resistive heaters, and ultrasound emitters.

As was mentioned briefly above, the step of delivering energy to the tissue, may involve, in some embodiments, the use of devices in which the one or more probes are actively or passively cooled. Cooling of probes can prevent the searing or coagulation of tissue directly adjacent to the probe(s) and can prevent the vaporization of liquid within the tissue. Cooling can also be used to increase the maximum lesion volume that can be formed in a given tissue.

In addition to optionally measuring impedance, as in the embodiment described above, some embodiments further comprise an additional step of measuring the temperature of tissue at least at one location. This is generally desirable so as to ensure that a given region of tissue is not exceeding a certain temperature. For example, in some embodiments it may be desirable to maintain the temperature of tissue at or below a temperature required for neural ablation. Preferably, a means for monitoring temperature may be located on or within a distal region of the one or more probes and the temperature of tissue located proximate to the distal region(s) of the probe(s) may be monitored using the means for monitoring temperature. Alternatively or in addition, a means for monitoring temperature may be located at a different location on the one or more probe(s) to monitor the temperature of a region of tissue located some distance away from the distal region(s) of the probe(s). Furthermore, one or more separate means for monitoring temperature may be inserted into the patient's body in order to monitor the temperature of one or more specific regions of tissue. The means for monitoring temperature may take the form of one or more thermocouples, thermistors, optical thermal sensors or any other means for monitoring or sensing temperature and the invention is not limited in this regard. The means for monitoring temperature may be connected directly to the energy source (e.g. the RF generator) or they may be monitored by an independent temperature monitoring device. These embodiments are intended to be exemplary only and are not intended to limit the present invention in any way.

As a feature of this aspect of the present invention, the method may further comprise one or more steps of modifying a treatment procedure in response to one or more measured parameters. These measured parameters may include, but are not limited to, temperature, position of the probe(s) or impedance, or any combination thereof. For example, if a temperature measurement is determined to be outside of a desired range, a treatment procedure may be modified by, for example, altering the amount of energy delivered by the generator, modifying or modulating the one or more means for cooling in some way, or terminating the procedure, as has been described with respect to the first aspect above. As another example, the amount of energy delivered by the generator may be modified based on the position of the one or more probes (for example, depending on the distance between a probe and the target treatment site or on the distance between the probes themselves when more than one probe is used). In such embodiments, a feedback system may be incorporated directly into the energy source so that any modification of a treatment procedure in response to a measured parameter may occur automatically. In other embodiments, there may not be an automatic feedback system in place, in which case a user may manually modify a treatment procedure in response to a measured parameter. In addition to modifying a treatment procedure based on measured parameters, this invention also provides for a step of determining the initial parameters to be used in a treatment procedure (for example, the initial maximum power level or tissue temperature, temperature ramp rate, etc.) using information that is known about the particular tissue to be treated. For example, if pretreatment testing reveals specific information about the sacrum of a particular patient (this information may include, but is not limited to: the topology of the sacrum, location of specific nerves, etc.), that information may be used to decide on what parameters to use initially for the treatment procedure.

In some embodiments of this aspect of the present invention, the step of performing a treatment operation in order to reduce symptoms associated with SIJS may comprise the addition or removal of material to or from the body. Material that may be added to the region of tissue being treated includes, but is not limited to, alcohol, chemical lysing agents, pharmaceutical agents (including, but not limited to, anesthetics or other medicaments) or contrast media. Material that may be removed from the region of tissue being treated includes, but is not limited to, ligamentous tissue or other connective tissue. The removal of material may be accomplished through various means, which can include aspiration or vaporization. Furthermore, the steps of addition and removal of material can be performed concurrently, for example by irrigating the tissue with a liquid medium while aspirating the liquid effluent. The addition or removal of material may also be combined with the delivery of energy, as has described above, wherein the delivery of energy and the addition or removal of material may occur concurrently or sequentially.

According to this aspect of the present invention, as has been described, one or more probes or other devices are placed at some location external to the SI joint. It should be understood that the probe(s) may be inserted into various locations and the invention is not limited in this regard. Furthermore, as has already been mentioned, a probe may be inserted using any approach that allows access to the desired tissue, including but not limited to: a superior posterior approach, an inferior posterior approach, or an anterior approach.

If more than one probe is used, the probes may be inserted into the tissue using different approaches. For example, when practicing this method aspect of the present invention using two probes in a bipolar configuration, as has been previously mentioned, the probes may be inserted at a relatively higher angle (i.e. closer to an anterior-posterior plane approach) with respect to the patient's body. When using probes in a bipolar configuration in this manner, it may be useful to follow a 'leapfrog' approach, wherein the two probes are inserted to initial locations and a lesion is created between the probes. Once the first lesion is created, the first probe is repositioned so as to be located on the other side of the second probe, for example more cephalad (towards the head) along the sacrum, and a second lesion is created. Following this, the second probe is repositioned so as to be located on the other side of the first probe, even more cephalad along the sacrum, and so on. This method can also be practiced by using a multiplicity of probes and leaving each probe in place. In other words, once a probe is in place it may remain there and further probes may be inserted in order to achieve this 'leapfrog' lesioning approach. In this way, an effective strip lesion may be created. In other embodiments, bipolar probes may be used in conjunction with various other approaches and this invention is not limited to using bipolar probes with this specific approach.

In embodiments of the present invention that employ more than one probe, the probes used during the course of a treatment procedure may form part of the circuit of an electrical impedance meter, as is known in the art, wherein energy may be transmitted between the probes through a region of tissue, allowing a user to determine the impedance of said region of tissue. This feature may be useful to determine whether or not the impedance of the tissue lies within a 'normal' range—if the impedance of the tissue is found to be outside that range, it may be indicative of an injury or defect within the tissue. As mentioned above, a single probe may also have an impedance measuring capability, for example to help determine the location of the probe within a patient's body.

Certain embodiments of the present invention may further comprise a step of performing a function to map the neural pathways in the tissue and this step may occur one or more times throughout the course of the procedure. The step of performing a function to map the neural pathways in the tissue can involve, in some embodiments, stimulation of the neural tissue at one or more physiological stimulation frequencies and subsequent observation to determine the effect of said stimulation. As is well known in the art, various frequencies and voltages can be used to stimulate both sensory and motor nerves, as has been described with respect to the first method aspect above. Observation of said stimulation can take the form of visual, sensory, mechanical, or electrical detection of muscle activity, or the form of sensory or electrical detection of nociceptive or other sensory neural activity (e.g. temperature). Using this step, it can be determined whether a target nerve or nerves has a function that would contraindicate its ablation or functional alteration. In some embodiments, the lack of a contraindication would lead to the step of delivering energy, whereas the presence of a contraindication would lead back to the step of inserting a probe or probes, whereby the step of inserting a probe or probes includes modifying the position of a probe or probes within the body.

Exemplary devices that may be used to perform the treatment methods described throughout this specification are described in co-pending applications: U.S. provisional application No. 60/593,839, filed Feb. 17, 2005; U.S. provisional application No. 60/594,787, filed May 5, 2005; U.S. provisional application No. 60/595,426, filed Jul. 4, 2005; U.S. provisional application No. 60/595,559, filed Jul. 14, 2005; and U.S. provisional application No. 60/595,560, filed Jul. 14, 2005.

The embodiments of the various aspects of the invention described above are intended to be exemplary only.

It is appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of treating the sacroiliac region of a patient's body by delivering energy through a single probe, comprising the steps of:
   positioning one elongated probe comprising at least one energy delivery device within a sacroiliac joint of the body; and
   delivering radiofrequency energy through the one elongated probe to create a lesion within the sacroiliac joint.

2. The method of claim 1, wherein energy is delivered sufficient to alter the function of at least one neural structure innervating the sacroiliac joint.

3. The method of claim 1, wherein the step of delivering radiofrequency energy comprises delivering energy through the one elongated probe sufficient to create a strip lesion within the sacroiliac joint.

4. The method of claim 3, wherein the strip lesion has its longest dimension parallel to a longitudinal axis of the elongated probe.

5. The method of claim 3, wherein the strip lesion is created while the one elongated probe remains in a substantially static position.

6. The method of claim 1, wherein the step of delivering radiofrequency energy comprises delivering energy along a substantial part of a long axis of the sacroiliac joint.

7. The method of claim 1, wherein energy is delivered in a configuration selected from the group consisting of a monopolar configuration, a bipolar configuration and a triphasic configuration.

8. The method of claim 1, wherein the at least one energy delivery device is actively or passively cooled.

9. The method of claim 1, wherein the radiofrequency energy is delivered in a series of amplitude or frequency modulated pulses.

10. The method of claim 1, wherein the one elongated probe comprises a resistive heater, whereby thermal energy may be delivered to the sacroiliac joint.

11. The method of claim 1, wherein the step of positioning the one elongated probe comprises positioning the one elongated probe within an intra-articular space of the sacroiliac joint.

12. The method of claim 1, wherein the step of positioning the one elongated probe comprises positioning the one elongated probe within a region of cartilage of the sacroiliac joint.

13. The method of claim 1, wherein the step of positioning the one elongated probe comprises inserting the one elongated probe through a synovial capsule of the sacroiliac joint.

14. The method of claim 1, wherein the step of positioning the one elongated probe comprises positioning the one elongated probe adjacent to at least one of the anterior and posterior margins of the sacroiliac joint.

15. The method of claim 1, wherein the step of positioning the one elongated probe comprises a step of using one or more introducers to penetrate into the sacroiliac joint.

16. The method of claim 15, wherein at least one of the one or more introducers are curved.

17. The method of claim 1, wherein the step of positioning the one elongated probe is facilitated using an imaging modality.

18. The method of claim 17, wherein the step of positioning the one elongated probe comprises visualizing at least one radiopaque marker to assess a position of the at least one energy deliver device within the body.

19. The method of claim 1, wherein the step of delivering radiofrequency energy comprises delivering energy sufficient to contract collagen.

20. The method of claim 1, wherein the step of delivering radiofrequency energy comprises delivering energy sufficient to reduce a volume of intra-articular space of the sacroiliac joint.

21. The method of claim 1, further comprising a step of delivering energy to stimulate at least one nerve at least one of before and after the step of delivering radiofrequency energy.

22. The method of claim 1, further comprising a step of measuring a parameter of the sacroiliac joint, wherein the measured parameter is selected from the group consisting of impedance, temperature and pressure.

23. The method of claim 22, further comprising a step of modifying a treatment procedure in response to the measured parameter.

24. The method of claim 23, wherein the step of modifying a treatment procedure comprises performing a treatment modification step selected from the group consisting of altering an amount of energy delivered by an energy source to the one elongated probe, modulating a means for cooling the one elongated probe, and terminating the treatment procedure.

25. The method of claim 23, wherein the step of modifying a treatment procedure is performed automatically in response to the measured parameter.

26. The method of claim 1, further comprising a step of removing material from the sacroiliac joint.

27. The method of claim 26, wherein the material is selected from the group consisting of synovial fluid, ligamentous tissue and cartilage.

28. The method of claim 1, further comprising a step of adding material to the sacroiliac joint.

29. The method of claim 28, wherein the material is selected from the group consisting of alcohol, chemical lysing agents, pharmaceutical agents, sealants, matrix molecules, electrolyte solutions, contrast media and any combination thereof.

30. The method of claim 1, further comprising the steps of repositioning the one elongated probe at a second position within the sacroiliac joint and delivering radiofrequency energy through the one elongated probe at the second position.

31. A method of treating the sacroiliac region of a patient's body by delivering energy through a single probe, comprising the steps of:
   positioning one elongated probe comprising at least one energy delivery device within a sacroiliac joint of the body; and
   delivering energy through the at least one energy delivery device of the one elongated probe to create a lesion within the sacroiliac joint.

32. The method of claim 31, wherein the energy is selected from the group consisting of electromagnetic energy, thermal energy and ultrasonic energy.

33. A method of treating the sacroiliac region of a patient's body by delivering energy, comprising the steps of:
   positioning at least one energy delivery device adjacent to a sacroiliac joint; and
   delivering radiofrequency energy through said at least one energy delivery device in a monopolar configuration to create a lesion at least partially within the sacroiliac joint.

34. The method of claim 33, wherein the step of positioning the at least one energy delivery device comprises positioning the at least one energy delivery device substantially along a posterior margin of the sacroiliac joint.

35. A method of treating the sacroiliac region of a patient's body by delivering energy, comprising the steps of:
   positioning at least one energy delivery device within a sacroiliac joint of the body, such that a long axis of the at least one energy delivery device is oriented along a long axis of the sacroiliac joint; and
   delivering radiofrequency energy through the at least one energy delivery device.

36. The method of claim 35, wherein the step of delivering energy comprises delivering energy substantially along a majority of the long axis of the sacroiliac joint.

* * * * *

UNITED STATES PATENT AND TRADEMARK OFFICE
CERTIFICATE OF CORRECTION

| | | |
|---|---|---|
| PATENT NO. | : 7,824,404 B2 | Page 1 of 1 |
| APPLICATION NO. | : 11/534907 | |
| DATED | : November 2, 2010 | |
| INVENTOR(S) | : Godara et al. | |

It is certified that error appears in the above-identified patent and that said Letters Patent is hereby corrected as shown below:

On page 2 of the Summary, Column 2:

Simon S. "Sacroiliac joint injection and low back pain", Interventional Pain Management, please delete "636-639" and insert --535-539--.

Response to Office Action for U.S. Appl. No. 11/280,604, "Mailed on May 12, 2009", please delete "Mailed on Dec. 11-12, 2009" and insert --Mailed on Nov. 12, 2009--.

Column 22, Line 54 after the word "device", please insert --to the sacroiliac joint.--.

Column 22, Line 56 after the word "energy", please delete "substantially".

Signed and Sealed this
Twenty-third Day of October, 2012

David J. Kappos
*Director of the United States Patent and Trademark Office*